United States Patent [19]

Marsden et al.

[11] Patent Number: 4,782,102

[45] Date of Patent: Nov. 1, 1988

[54] NOVEL ORGANOFUNCTIONAL SILANES CONTAINING HINDERED GROUP

[75] Inventors: James G. Marsden, Rowayton; Herbert E. Petty, Bethel, both of Conn.; Anthony C. Vecere, White Plains; Patrick Morabito, Mt. Vernon, both of N.Y.

[73] Assignee: Union Carbide Corporation, Danbury, Conn.

[21] Appl. No.: 763,320

[22] Filed: Aug. 7, 1985

Related U.S. Application Data

[62] Division of Ser. No. 452,938, Dec. 27, 1982, abandoned.

[51] Int. Cl.⁴ ............................ C08K 3/36; C08L 61/06
[52] U.S. Cl. ........................................ 523/143; 523/144; 523/145; 523/139; 524/540; 524/594; 524/549; 525/342
[58] Field of Search ................ 525/342; 523/144, 145, 523/143; 524/188

[56] References Cited

U.S. PATENT DOCUMENTS

| | | | |
|---|---|---|---|
| 2,832,754 | 4/1958 | Jex et al. | 260/46.5 |
| 2,930,809 | 3/1960 | Jex et al. | 260/448.8 |
| 3,321,350 | 5/1967 | Fekete | 556/413 |
| 3,403,721 | 10/1968 | Robins et al. | 164/43 |
| 3,409,579 | 11/1968 | Robins et al. | 260/30.4 |
| 3,414,604 | 12/1968 | Pepe et al. | 556/413 X |
| 3,477,901 | 11/1969 | Keil | 556/413 X |
| 3,487,043 | 12/1969 | Grudus | 525/342 |
| 3,772,351 | 11/1973 | Krahnke | 556/421 |
| 3,808,172 | 4/1974 | Albarino et al. | 556/413 X |
| 3,864,373 | 2/1975 | Seller et al. | 260/448.8 |
| 4,243,767 | 1/1981 | Kaufman | 525/342 |
| 4,247,354 | 1/1981 | Ward et al. | 525/342 |
| 4,256,623 | 3/1981 | Junger et al. | 164/43 |

FOREIGN PATENT DOCUMENTS 1143351  2/1969  United Kingdom ............... 523/144

*Primary Examiner*—Lewis T. Jacobs
*Attorney, Agent, or Firm*—Eugene C. Trautlein

[57] ABSTRACT

A novel organofunctional silane for use in binding agent compositions employed in foundry sands and the cores and molds made therefrom. The novel organofunctional silane is characterized in that it contains at least one sterically hindered hydrocarbon group and has attached to the silicon atom a nitrogen containing group via a carbon-silicon bond.

14 Claims, No Drawings

NOVEL ORGANOFUNCTIONAL SILANES CONTAINING HINDERED GROUP

This application is a division of prior U.S. application Ser. No. 452,938, filed 12/27/82, now abandoned.

BACKGROUND OF THE INVENTION

This invention relates to novel organofunctional silanes and their use in binding agent compositions for foundry sands. More particularly, this invention relates to organofunctional silanes that contain at least one hindered alkoxy group and its use in binding agent compositions having especially good shelf life.

It is well known in the art that one can impart general improved strengths and increased humidity resistance to foundry cores by adding a silane compound to the resinous foundry binder used to form the cores. Foundry cores made with such resinous binders as phenolic/isocyanate systems, furan systems, oil modified polyol/polyisocyanate systems, phenolic resins and urea/phenolic resins have a tendency to lose strength and become weak upon exposure to humid conditions. As illustrated by U.S. Pat. Nos. 3,409,579 and 3,403,721, silane compounds have been added to such resinous binders to increase the humidity resistance and general strength of foundry cores made with these binders. Aqueous dispersions of silane compounds have also been used as binders themselves (see U.S. Pat. No. 3,093,494).

It is known that aminoalkyl trialkoxysilanes, such as -aminopropyltrimethoxysilane, improve the adherence of thermosetting resins to inorganic oxide materials. It is furthermore known that these amino-silanes can be mixed with thermosetting phenolic resins and then the resulting mixtures can be mixed directly with sands or other inorganic oxide material to be shaped and solidified (cf. DE-AS No. 1,252,853 and DE-PS No. 1,494,381).

The use of N-(aminoalkyl)-aminoalkylsilanes as adhesion improvers between thermosetting resins and inorganic oxide material is also known. These compounds are used in the same manner as the above-mentioned aminosilanes in which there is no substitution on the nitrogen atom (cf. U.S. Pat. No. 3,234,159).

Both the aminoalkylsilanes which are not substituted on the nitrogen atom and those which are substituted by aminoalkyl groups, all of which are referred to hereinafter as aminosilanes, improve the adhesion of thermosetting phenolic resins to inorganic oxide substances to virtually the same degree when they are mixed with the resins. This improvement of adhesion, however, diminishes in the course of time if these aminosilane-containing resins are stored for a relatively long time at room temperature. U.S. Pat. No. 4,256,623 reports that, after standing for only 14 days, for example, the adhesion-improving action of aminosilanes declines by about 40%, and at the end of only a month the adhesivizing effect produced by 3-aminopropyltriethyxysilane in phenolic resin has been reduced by one half.

It has been further reported that the loss of the adhesivizing action of the aminosilanes in mixture with thermosetting resins is probably due to a decomposition of these silanes in the resins. Therefore, there existed the problem of finding an adhesivizing agent which, when mixed with thermosetting resins, decomposes very slightly or not at all, and produces its adhesivizing action to the same or an only slightly lesser extent, even after the resin has been stored for a relatively long time and which therefore will be useful in the preparation of binding agents for inorganic oxide materials such as, for example, foundry sands, such binding agents being made from ureido-functional silanated phenolic resins whose strength enhancing effectiveness will remain unaltered or only slightly reduced, even after a relatively long period of storage.

U.S. Pat. Nos. 3,671,562; 3,754,971 and 4,046,794 disclose ureido-functional organosilicon compounds and the use of same as coupling agents on inorganic substrates such as glass, clay, silica, hydrated silica, fumed silica, sand, e.g., foundry sand and the like. U.S. patent application No. 309,657 filed Oct. 8, 1981 described ureido-functional organosilicon compounds having two hydrolyzable or hydroxy groups and in which at least one ureido-functional group is connected to silicon by groups containing at least five carbon atoms which are also useful as binding agents.

Despite repeated advances in the art there continues to remain the need to seek out and identify novel materials useful as binding agents which will impart good shelf life to the composition. It is believed that this invention fulfills this task and represents an advance over the existing art.

SUMMARY OF THE INVENTION

The present invention provides novel organofunctional silane selected from the group consisting of silanes of the formula:

$$ZSiR_a(OR')_b(OR'')_c$$

wherein R is individually an alkyl, aryl, alkaryl or aralkyl group containing from one to twelve carbon atoms inclusive; R' is selected from the group consisting of $-CH_3$, $-C_2H_5$, $-C_3H_7$ and $-CH_2CH_2OCH_3$; R'' is a sterically hindered hydrocarbon group; Z is a nitrogen containing group bonded to the silicon atom via a carbon-silicon bond; a and b are individually integers with a value of 0, 1 or 2; and c is an integer with a value 1, 2 or 3 wherein the sum of a+b+c equals 3.

The present invention also provides a use of said novel organofunctional silanes in binding agent compositions for foundry sands. Such binding agent compositions have excellent shelf life and can be used with inorganic fillers or oxides for the purpose of imparting improved strength of shapes.

DESCRIPTION OF THE INVENTION

In accordance with the present invention there is provided a novel class of organofunctional silanes useful in binding agent compositions. It has been found, quite unexpectedly, that the use of organofunctional silanes containing at least one hindered alkoxy group will provide significantly greater performance stability when added to a curable binder, such as a hardenable resin, than would the corresponding non-hindered organofunctional silane.

The organofunctional silane of the present invention can be prepared by reacting known organosilicon compounds. Examples of such reactions include, but may not necessarily be limited to:

$$ZSiR_a(OR')_{3-2} + CHOR'' \longrightarrow ZSiR_a(OR')_b(OR'')_c + CHOR' \qquad (1)$$

$$N\equiv C(CH_2)SiR_a(OR')_b(OR'')_c + H_2 \longrightarrow \quad (2)$$
$$NH_2CH_2(CH_2)_x - SiR_a(OR')_b(OR'')_c$$

$$HSiR_a(OR')_b(OR'')_c + NH_2CH_2CH=CH_2 \xrightarrow{cat} \quad (3)$$
$$NH_2(CH_2)_3SiR_a(OR')_b(OR'')_c$$

$$Cl(CH_2)_xSiR_a(OR')_b(OR'')_c + 2NH_3 \longrightarrow \quad (4)$$
$$NH_2(CH_2)_xSiR_a(OR')_b(OR'')_c + HCl$$

The reactions set forth above are generally described in U.S. Pat. Nos. 2,832,754; 2,930,809; and 3,864,373. Because of the variety of known techniques for preparing organofunctional silanes suitable reactants will depend upon which reaction path is ultimately chosen. Reference to these patents and other known methods for preparing organofunctional silanes will identify useful reactants.

The resulting organofunctional silane is of the general formula:

$$ZSiR_a(OR')_b(OR'')_c$$

wherein R is individually an alkyl, aryl, alkaryl or aralkyl group containing from one to twelve carbon atoms inclusive. Preferably, R is individually an alkyl group containing from one to four carbon atoms. R' is individually selected from the group consisting of —CH$_3$, —C$_2$H$_5$, —C$_3$H$_7$ and —CH$_2$CH$_2$OCH$_3$, preferably R' is individually —C$_2$H$_5$. R" is a sterically hindered hydrocarbon group, such groups include —C(CH$_3$)$_3$, —C(CH$_2$CH$_3$)$_3$, —CH$_2$C(CH$_3$), —CH$_2$CH$_2$C(CH$_3$)$_2$, —C(CH$_2$CH$_2$CH$_3$)$_3$ and the like. Preferably, R" is —C(CH$_3$)$_3$. The values of a and b are individually 0, 1 or 2 and c is an integer with a value of 1, 2 or 3. The sum of a+b+c must equal 3 and it is preferred that a=o, b=2 and c=1. Z is any nitrogen containing group bonded to the silicon atom via a carbon-silicon bond. Preferably Z is of the general formula NH$_2$CH$_2$CH$_2$CH$_2$—.

Suitable organofunctional silanes having at least one hindered alkoxy group include, but are not necessarily limited to, NH$_2$CH$_2$CH$_2$CH$_2$Si(OtBu)(OEt)$_2$
NH$_2$CH$_2$CH$_2$NHCH$_2$CH$_2$CH$_2$Si(CH$_3$)(OtBu)$_2$
NH$_2$CH$_2$CH$_2$CH$_2$NHCH$_2$CH$_2$CH$_2$Si(OtBu)$_2$(OMe)
NH$_2$CH$_2$CH$_2$NHCH$_2$CH$_2$NHCH$_2$CH$_2$CH$_2$Si(OtBu)(OMe)$_2$
NH$_2$C(O)NHCH$_2$CH$_2$CH$_2$Si$_2$(CH$_3$)(OtBu)$_2$
NH$_2$C(O)NHCH$_2$CH$_2$NHCH$_2$CH$_2$CH$_2$Si(OtBu)$_2$(OEt)
NH$_2$CH$_2$CH(CH$_3$)Si(OtBu)$_3$

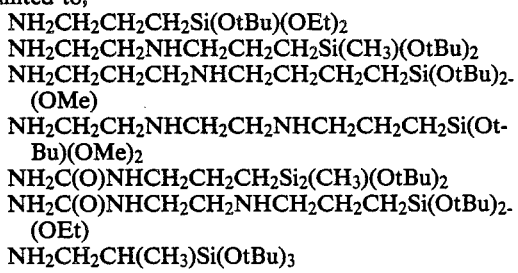

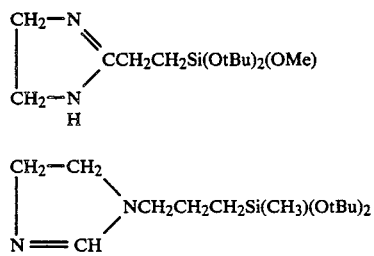

This invention is also directed to improvements in foundry sands and foundry cores and molds made therefrom. The foundry sands useful in the present invention are conventional foundry sands such as silica sands having a high silica content, for example a silica content of at least 80% by weight. Examples of such foundry sands are (1) white silica sands such as Wedron White Silica sand, (99.8% by weight silica), Ottawa White Silica sand (99.8% silica), Minnesota White Silica sand (98.5% silica); (2) lake sands, such as Port Cresent sand (95.0% silica), Manley 20KK sand (91.9% silica), Nugent Lake sand (94.2% silica), Lake Shore sand (93.5% silica); and (3) banks sands such as Juniada Bank sand (90.2% silica). These foundry sands normally have a Grain Fineness Number (GFN) of about 50 to 90, as determined by the standard AFS method.

Other inorganic oxides or fillers can be bound by the binding agents pursuant to this invention and they include any suitable fibrous or particulate inorganic substance. At the time of mixing the binding agent with the fillers, the fillers may be in the form of particles, spherical or approximately isometric, or they may be in the form of plates or needles (fibers). The size of the filler particles is not critical, any of the conventionally used fillers being suitable in this respect. Among the specific fillers which may be used in the present invention are asbestos, ground glass, kaolin and other clay minerals, silica, calcium silica, magnesium oxide, barium carbonate, bariumsulfate (barytes), metal fibers and powders, glass fibers, refractory fibers, non-reinforcing carbon blacks, titanium dioxide, mica, talc, chopped glass, alumina, quartz, wollastdonite (calcium silicate), and inorganic coloring pigments.

The curable binders useful in the binding agent compositions of this invention are polymerizable or thermosetting to form three-dimensional structures and are capable of binding the inorganic oxide or filler into a shaped mass. Included as examples of suitable curable binders are the foundry binders or hardenable resins which when used with the above ureido-functional silicon compounds of this invention show improved strength or resistance to humidity in the foundry core. Generally these foundry binders are the phenolic/polyisocyanate binder systems such as described in U.S. Pat. No. 3,409,579; furan binder systems such as described in U.S. Pat. No. 3,346,534; oil modified polyol/polyisocyanate binder systems such as described in U.S. Pat. No. 3,255,500; and phenolic and urea/phenolic resin binder systems such as described in U.S. Pat. Nos. 3,404,198 and 3,306,864.

Further illustrative of resins which can be effectively bonded include the thermosetting resins, such as the phenol formaldehyde resin, melamine-formaldehyde resins, alkyl resins, polyurethane resins, epoxy resins, and the like.

More broadly, the invention can be applied to substantially any polymeric material in which improved adhesion to fillers or inorganic oxides is desired, including, for example, any of the rubbers, resins if plastics with which fillers, e.g., inorganic oxides, are conventionally employed. Such polymers include natural rubber; synthetic rubbers such as styrene-butadiene rubber; ethylene-propylene terpolymer rubber; urethane rubbers; polyolefins such as polyethylene, polypropylene, and polyisobutylene; poly-acrylonitrile; polybutadiene; copolymers of butadiene and acrylonitrile; polystyrene; poly(styreneacrylonitrile); copolymers of styrene with butadiene and acrylonitrile; copolymers of ethylene with propylene or butene-1 or vinyl acetate or maleic anhydride; polycarbonate resins; phenoxy resins, polyvinyl chloride; copolymers of vinyl chloride with vinyl acetate or other vinyl esters; polyvinyl acetate; linear polyesters; polyvinyl acetals; polyvinylidene chloride; copolymers of vinylidene chloride with vinyl chloride and acrylic acid; poly(methyl methacrylate); superpolyamides, e.g. nylon; polysulfones; allyl resins such as a polymer of diallyl phthalate; epoxy resins, phenolic resins; silicone resins; polyester resins including alkyl resins; poly(vinylacetate-vinyl chloride); poly(vinylidene chloride); thermoplastic polyurethanes; thermoplastic polyhydroxy ethers; thermoplastic polyesters; poly(vinyl chloride-maleic anhydride); and others. Preferred polymeric matrices are the thermosetting or curable resins, such as the hardenable foundry sand resins as described above, and the like.

The proportions of the organofunctional silane compound and curable binder in the novel binding agent compositions of this invention can be varied over a wide range. For example, the novel compositions can contain from about 0.01 to about 5, preferably about 0.05 to about 2, weight parts of the organofunctional silane compound per 100 weight parts of curable binder. The proportions of binding agent composition and sand used in making the novel foundry sand compositions of this invention can be varied over a wide range and are generally the same respectively as the proportions of coupling agent and sand conventionally employed in the art. While the organofunctional silane compounds can be employed undiluted, it usually is more convenient to employ them as solutions, e.g., 25 to 95%, in suitable solvents such as methanol, ethanol, isopropanol and the like because such solutions are easier to handle and disperse in the curable binder. They may also be mixed with other organofunctional silanes that do not contain a hindered alkoxy group provided the compounds are compatible and do not react to create any undesirable by products.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

PREPARATION OF STERICALLY HINDERED ALKOXY SILANES

Example I

Into a 500 ml 3-necked flask equipped with a magnetic stirrer, heating mantle, thermometers, a 12 in. distilling column packed with ⅛ in. glass helices, addition funnel, distilling head and receiver was added 179.3 g (1.0 mole) of 3-aminopropyltrimethoxysilane. The flask was heated to 160° C. and from the (heated) addition funnel 160 g (2.16 moles) of t-butanol was slowly added with the simultaneous distillation of methanol/t-butanol to the receivers. The rate of addition of t-butanol was kept slow in order to maintain as high a flask temperature as possible (150°–170° C). Periodic sampling of the flask and lites for gas chromotograph analysis indicated that after 2.16 moles t-butanol had been added, approximately an 80% conversion of 3-aminopropyltrimethoxysilane to Compound A* had been achieved. Distillation of this material with four cuts (94°–100° C. at 20 mm Hg) produced 100 g of 94% pure aminopropyl-t-butoxydimethoxysilane (combined cuts 2, 3, 4). Cut one, enriched in 3-aminopropyltrimethoxysilane was 30 grams.

Example II

Using the procedure described in Example I, 3-aminopropyltriethoxysilane (1.0 mole) was reacted with t-butanol (5.0 moles) to convert 60% of the 3-aminopropyltriethoxysilane to Compound B*. This mixture was distilled and three cuts were made.

| Cut Number | Weight | Temperature/ Pressure | 3-amino propyl triethoxy silane | Compound B |
|---|---|---|---|---|
| 1 | 85 g | 92° C./ 7.5 mm Hg | 60% | 35% |
| 2 | 20 g | 95° C./ 7.5 mm Hg | 20% | 90% |
| 3 | 76.5 g | 96° C./ 6.5 mm Hg | 3% | 94% |

Example III

An alternate process, indicated that when 165.9 g (0.75 moles) of 3-aminopropyltriethoxysilane and 55.6 g (0.75 moles) of t-butanol were heated together in a 300 cc rocking autoclave for 4.5 hours at 165°–180° C., a 15% conversion to Compound B was realized.

TABLE I

| Compound | Composition |
|---|---|
| A | $NH_2CH_2CH_2CH_2Si(OC[CH_3]_3)(OCH_3)_2$ |
| B | $NH_2CH_2CH_2CH_2Si(OC[CH_3]_3)(OC_2H_5)_2$ |

EXPERIMENTAL PROCEDURE

Into a suitable vessel there is charged a commercially available furan type resin. Thereafter there is added 0.03 grams (0.2%, based on the resin) of an organofunctional silane. The mixture is blended for 2–4 hours and evaluated (initial evaluation).

The blended mixture is then allowed to age at room temperature.

Then 1500 grams of AFS testing Sand 50–70 are charged into a different vessel. The contents are mixed at a slow speed as 0.75–1.50 gram s (0.05–0.1% based on the sand) of water and 3.75–6.0 grams (25–40% based on the resin) of a commercially available catalyst are added separately via syringe. The contents are further mixed for two (2) minutes. To this second vessel there is added, via syringe, 15 grams (1% based on the sand) of the resin neat or the resin/silane prepared in the first vessel. Mixing is continued for two (2) minutes. Immediately following mixing the molds were filled without compacting. The sand mixture is then pressed firmly into the mold with a #14 rubber stopper. The mold is then smoothed off with trowel and allowed to stand 24 hours.

Tensile strength is tested using a jug designed for briquet testing (ASTM C-190-63). The cross-head speed is 0.2 inches per minute.

The improved performance, particularly after aging of the resin/silane blend, provided by the organofunctional silane of this invention is demonstrated in the following examples. This data show the tensile strength of sand/resin composites prepared within hours of adding the organofunctional silane to the resin and after the resin/silane blend has aged six months at room temperature.

TABLE III

| Organofunctional Silane | Resin | Catalyst | Tensile Strength, psi Initial | 6 mo. @ R.T. |
|---|---|---|---|---|
| $NH_2CH_2CH_2CH_2Si(OCH_3)_3$ | Borden Thor | BSA 40% BOR | 213 | 75 |
| Silane A | Borden Thor | BSA 40% BOR | 211 | 186 |
| $NH_2CH_2CH_2CH_2SI(OC_2H_5)_3$ | Borden Thor | BSA 40% BOR | 195 | 119 |
| Silane B | Borden Thor | BSA 40% BOR | 182 | 168 |
| $NH_2CH_2CH_2CH_2SI(OCH_3)_3$ | Acme 931 | TSA 25% BOR | 282 | 166 |
| Silane A | Acme 931 | TSA 25% BOR | 303 | 266 |
| $NH_2CH_2CH_2CH_2Si(OC_2H_5)_3$ | Delta 632X | BSA 30% BOR | 201 | 89 |
| Silane B | Delta 632X | BSA 30% BOR | 309 | 159 |

PREPARATION OF 3-AMINOPROPYLMETHOXYD I-t-BUTOXYSILANE

Example IV

Into a one liter, 3-necked, round-bottom flask equipped with a distillation column and head, and protected with a nitrogen blow-by, mechanical stirrer, heating mantle and thermometers was added 268.8 g (1.5 moles) of 3-aminopropyltrimethoxysilane, 444.6 g (6.0 moles) of t-butanol and 10.8 g of a 25 wt. % solution of sodium methoxide in methanol. The resulting solution was heated to reflux (81°–100° C.) and a mixture of methanol and t-butanol was removed by fractional distillation over three hours. Gas chromatography indicated an 83% conversion of the starting silane to the mono-t-butoxy derivative. Continued distillation of the alcohol mixture over an additional 6 hours produced by gas chromatography a 14% conversion of the mono-t-butoxydimethoxysilyl derivative to the di t-butoxy component. An additional 7.5 moles (333.3 g) of t-butanol was added over 16 hours in increments of 3.5 moles, 1.0 mole and 3.0 moles while continuously removing methanol/t-butanol as a distillate. A total of 967.0 g distillate was collected to a flask temperature of 130° C. A gas chromatography of a sample of the flask contents indicated 85% contained 3-aminopropyldi-t-butoxymethoxysilane. Vacuum distillation yielded 54.0 g forecut, 30.0 g residue, and 293.2 g of distillate which, by gas chromatographic 13C NMR analyses, was 94% 3-aminopropyldi-t-butoxy-methoxysilane and 6% 3-aminopropyl-t-butoxydimethoxysilane.

PREPARATION OF 3-AMINOPROPYLDIMETHOXY-t-BUTOXYSILANE

Example V

Into a one liter, 3-necked, round-bottom flask equipped with a distillation column and head (protected with a dry nitrogen blow-by), mechanical stirrer, thermometers, and heating mantle, was added 358.4 g (2.0 moles) of 3-aminopropyl-trimethoxysilane, 296.4 g (4.0 moles) of t-butanol, and 2.9 ml of 40% (in methanol) benzyltrimethylammonium methoxide (BMAM). The resulting solution was heated to reflux (flask temperature 90°–100° C., head temperature 78°–82° C.) and over 3 hours removed 264.0 g of a mixture of methanol and t-butanol. An additional mole (74.1 g) of t-butanol and 3.6 ml of 40% BMAM was added with continued heating and removal of the alcohol mixture by distillation. A sample taken from the flask showed a 74% conversion of the original silane to the mono t-butoxy derivative by gas chromatography and nuclear magnetic resonance (13C) analyses. The contents of the flask were cooled, an additional 296.4 g (4.0 moles) of t-butanol and 3.6 ml of 40% BMAM were added, and the flask again heated and the methanol/t-butanol mixture removed by distillation. Re-examination of the flask contents indicated an increase to 81% conversion to the mono t-butoxy derivative by gas chromatography. No other products were detected. Distillation of the flask contents produced a distillation fraction, 238 g (boiling point, 85°–86° C. at 6 mm Hg), which was 96% 3-aminopropyldimethoxy-t-butoxysilane (4% 3-aminopropyltrimethoxysilane) by gas chromatographic analysis. A 13C NMR spectrum confirmed the structure.

We claim:

1. A binding agent for an inorganic oxide or filler material comprising a curable binder and an organofunctional silane, the improvement wherein the organofunctional silane is selected from the group of silanes of the general formula:

$ZSiR_a(OR')_b(OR'')_c$ wherein R is individually an alkyl, aryl, alkaryl or aralkyl group containing from one to twelve carbon atoms inclusive; R' is individually selected from the group consisting of $-CH_3$, $-CH_3H_7$, and $-CH_2CH_3OCH_3$; R'' is individually a sterically hindered hydrocarbon group; Z is a nitrogen containing group bonded to the silicon atom via a carbon-silicon bond; a and b are individually integers with a value of 0, 1 or 2; and c is an integer with a value of 1, 2 or 3 wherein the sum of a+b+c equals 3.

2. A binding agent for an inorganic oxide or filler material comprising a curable binder and an organofunctional silane, the improvement wherein the organofunctional silane is selected from the group of silanes of the general formula:

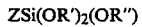
$ZSi(OR')_2(OR'')$ wherein R' is selected from the group consisting of $-CH_3$, $-C_2H_5$, $-C_3H_7$, and $-CH_2CH_3OCH_3$; R'' is a sterically hindered hydrocarbon group; and Z is a nitrogen containing group bonded to the silicon atom via a carbon-silicon bond.

3. The binding agent composition of claim 2 wherein the organofunctional silane is 3-aminopropylenethoxy-1-t-butoxysilane.

4. The binding agent composition of claim 1 wherein R is individually an alkyl group containing from one to four carbon atoms.

5. The binding agent composition of claim 1 wherein R' is individually $-C_2H_5$.

6. The binding agent composition of claim 1 wherein R'' is individually selected from the group of hindered hydrocarbon groups consisting of $-C(CH_3)_3$;

—CH$_2$C(CH$_3$)$_3$; —CH$_2$CH$_2$C(CH$_3$)$_3$; —C(CH$_2$CH$_3$)$_3$; and —C(CH$_2$CH$_2$CH$_3$)$_3$.

7. The binding agent composition of claim 6 wherein R″ is individually —C(CH$_3$)$_3$.

8. The binding agent composition of claim 1 wherein Z is NH$_2$CH$_2$CH$_2$CH$_2$—.

9. The binding agent composition of claim 1 wherein Z is —(CH$_2$)$_x$NH(CH$_2$)$_y$NH$_2$ wherein x and y are individually integers of from 1 to 5.

10. The binding agent composition of claim 1 wherein Z is —(CH$_2$)$_x$NHOCNH$_2$ wherein x is from 1 to 5.

11. The binding agent composition of claim 1 wherein a=0, b-2, and c-1.

12. The organofunctional silane of claim 2 where in R′ is —C$_2$H$_5$.

13. The organofunctional silane of claim 2 wherein R″ is —C(CH$_3$)$_3$.

14. The organofunctional silane of claim 2 wherein Z is —CH$_2$CH$_2$CH$_2$NH$_2$.

* * * * *